United States Patent
Someda

(10) Patent No.: US 10,413,193 B2
(45) Date of Patent: Sep. 17, 2019

(54) PHOTOACOUSTIC APPARATUS

(71) Applicant: CANON KABUSHIKI KAISHA, Tokyo (JP)

(72) Inventor: Yasuhiro Someda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 814 days.

(21) Appl. No.: 14/946,636

(22) Filed: Nov. 19, 2015

(65) Prior Publication Data

US 2016/0073888 A1 Mar. 17, 2016

Related U.S. Application Data

(63) Continuation of application No. 12/908,232, filed on Oct. 20, 2010, now Pat. No. 9,226,662.

(30) Foreign Application Priority Data

Oct. 29, 2009 (WO) .................. PCT/JP2009/068614

(51) Int. Cl.
*A61B 5/00* (2006.01)
*A61B 8/08* (2006.01)
*G01N 21/17* (2006.01)

(52) U.S. Cl.
CPC .......... *A61B 5/0095* (2013.01); *A61B 5/0059* (2013.01); *A61B 5/0062* (2013.01);
(Continued)

(58) Field of Classification Search
CPC .... G01N 21/1702; A61B 8/08; A61B 5/0059; A61B 5/0095; A61B 2576/00; A61B 5/0062

See application file for complete search history.

(56) References Cited

U.S. PATENT DOCUMENTS 6,212,421 B1 * 4/2001 Vo-Dinh .............. A61B 5/0091
600/407
2005/0070803 A1 3/2005 Cullum et al.

FOREIGN PATENT DOCUMENTS

CN 1373362 A 10/2002
CN 1462609 A 12/2003
(Continued)

OTHER PUBLICATIONS

Lihong V. Wang, "Tutorial on Photoacoustic Microscopy and Computed Tomography", 2008, vol. 14, p. 171-179.*
(Continued)

*Primary Examiner* — Patrick Assouad
*Assistant Examiner* — Haidong Zhang
(74) *Attorney, Agent, or Firm* — Canon U.S.A., Inc., IP Division

(57) ABSTRACT

In a photoacoustic apparatus, a light source irradiates an inspection target with pulsed light; a detector detects acoustic waves generated in the inspection target due to interaction of the pulsed light with the inspection target, and outputs detection signals corresponding to the detected acoustic waves; a light-quantity measurement unit measures the quantity of the light output from the light source; and a signal processor obtains information on an inside of the inspection target by using the detection signals output from the detector. The signal processor also corrects intensities of the detection signals so as to suppress variations in intensities of the detection signals caused by a temporal change in the quantity of the light.

31 Claims, 7 Drawing Sheets

(52) U.S. Cl.
CPC .......... *A61B 8/08* (2013.01); *G01N 21/1702* (2013.01); *A61B 2576/00* (2013.01)

(56) References Cited

FOREIGN PATENT DOCUMENTS

| | | |
|---|---|---|
| CN | 1883379 A | 12/2006 |
| WO | 2007/100937 A2 | 9/2007 |

OTHER PUBLICATIONS

Li, M., et al., "Simultaneous Molecular and Hypoxia Imaging of Brain Tumors In Vivo Using Spectroscopic Photoacoustic Tomography", Proceedings of the IEEE, Mar. 2008, pp. 481-489, vol. 96, No. 3.

Sivaramakrishnan, M., et al., "Limitations of quantitative photoacoustic measurements of blood oxygenation in small vessels", Phys. Med. Biol., Feb. 8, 2007, pp. 1349-1361, No. 52.

Zhang, H.F., et al., "Laser-scanning optical-resolution photoacoustic microscopy", Photons Plus Ultrasound: Imaging and Sensing, Proc. of SPIE, 2009, pp. 71770L-1-71770L-6, vol. 7177.

Rajian, J.R., et al., "Quantitative photoacoustic measurement of tissue optical absorption spectrum aided by an optical contrast agent", Optics Express, Mar. 16, 2009, pp. 4879-4889 vol. 17, No. 6.

Zhang, H.F., et al., "In vivo imaging of subcutaneous structures using functional photoacoustic microscopy", Nature Protcols, 2007, pp. 797-804, vol. 2, No. 4.

\* cited by examiner

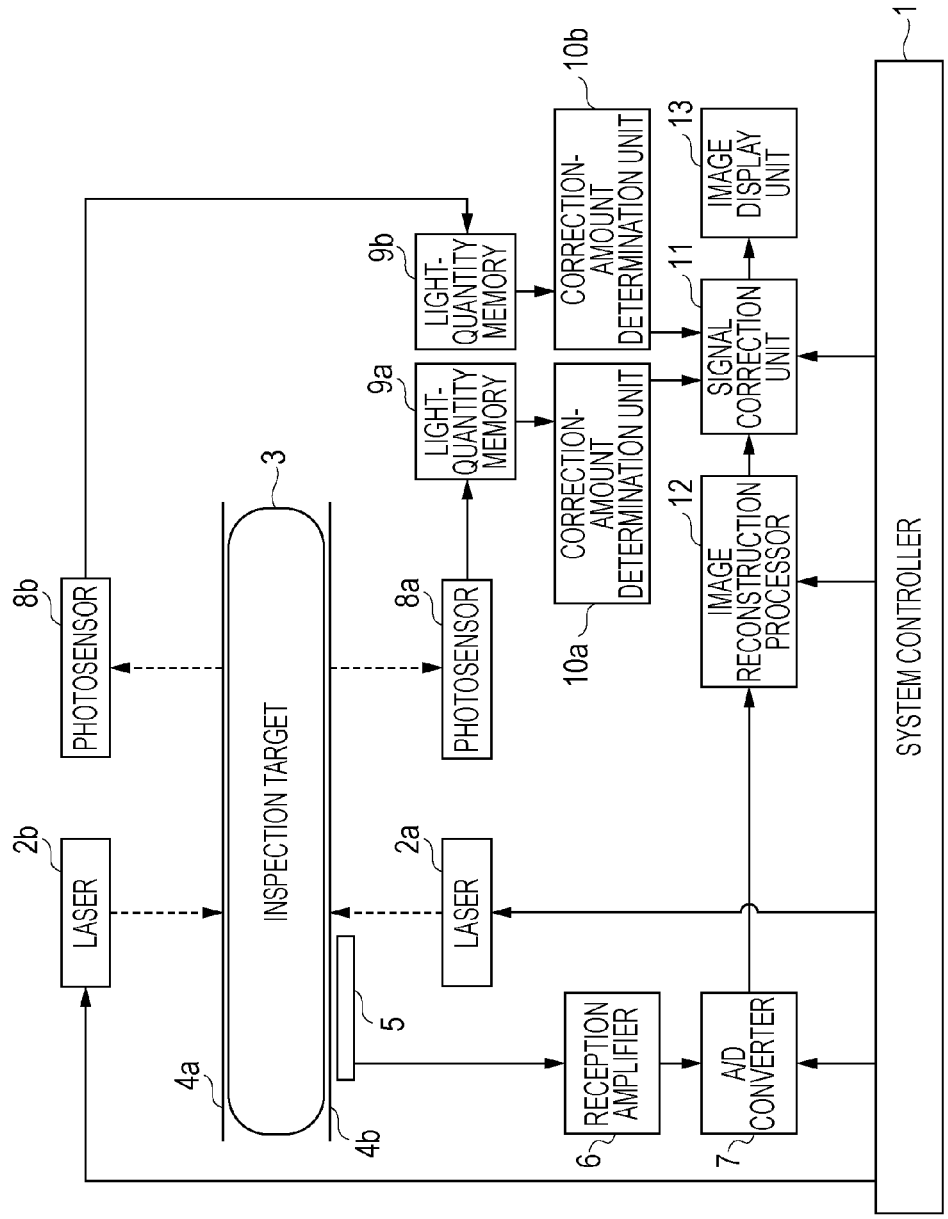

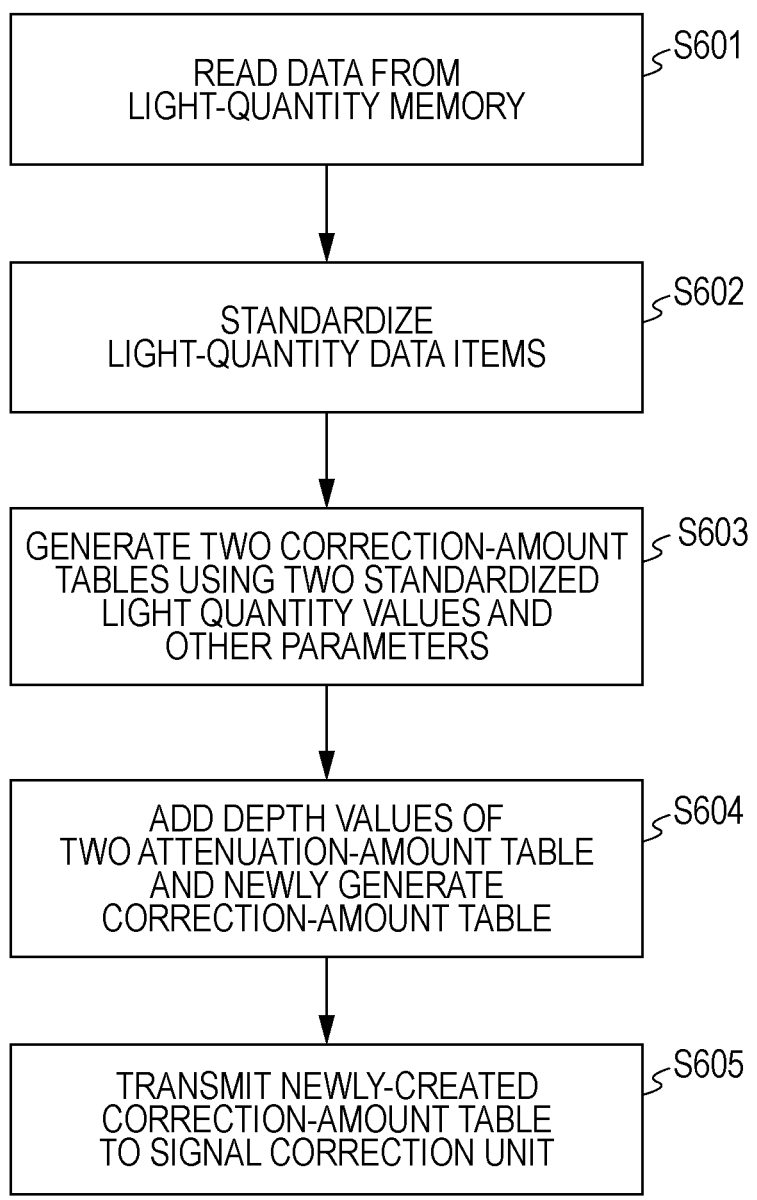

PHOTOACOUSTIC APPARATUS

CROSS-REFERENCE TO RELATED APPLICATIONS

This application is a Continuation of co-pending U.S. patent application Ser. No. 12/908,232 filed Oct. 20, 2010, which claims priority benefit from International Application No. PCT/JP2009/068614, filed Oct. 29, 2009. The disclosures of the above-named applications are hereby incorporated by reference herein in their entirety.

TECHNICAL FIELD

The present invention relates to a photoacoustic apparatus which irradiates an inspection target with light so that photoacoustic waves are generated and which receives the photoacoustic waves.

BACKGROUND ART

An optical imaging apparatus which irradiates a living body with light and which images information on an inside of the living body obtained in accordance with the incident light has been actively researched in a medical field. An example of such an optical imaging technique includes photoacoustic tomography (PAT). In photoacoustic tomography, a living body is irradiated with pulsed light generated from a light source so that acoustic waves generated from body tissues which absorb energy of the pulsed light which is propagated and dispersed in the living body are detected. One example of such a technique is described in U.S. Pat. No. 5,840,023 entitled "Optoacoustic Imaging for Medical Diagnosis" (hereafter "Patent Literature 1"). Specifically, elastic waves, that is, photoacoustic waves, generated when a detection target absorbs the irradiated light energy and therefore is momentarily expanded are received by a transducer by utilizing a difference between an optical energy absorption rate of the detection target such as a tumor and optical energy absorption rates of other tissues. By performing analysis processing on the detection signals, an optical characteristic distribution, and especially, an optical-energy absorption density distribution are obtained. This information may be used for quantitative measurement of a specific substance included in the inspection target such as glucose and hemoglobin included in blood, for example. Accordingly, the photoacoustic tomography may be utilized to specify a portion which includes a malignant tumor and growing new blood vessels.

Furthermore, Lihong V. Wang in "Tutorial on Photoacoustic Microscopy and Computed Tomography" (hereafter "Non Patent Literature 1") discloses an example of a case where a photoacoustic microscope is employed for photoacoustic imaging (PAI). According to Non Patent Literature 1, ultrasonic waves obtained by irradiating an inspection target with pulsed light are received by a transducer which performs imaging. Furthermore, by changing a wavelength of the pulsed light, spectroscopic characteristics of the inspection target are imaged.

CITATION LIST

Patent Literature

PTL 1 U.S. Pat. No. 5,840,023

Non Patent Literature

NPL 1 Lihong V. Wang "Tutorial on Photoacoustic Microscopy and Computed Tomography", IEEE Journal of Selected Topics in Quantum Electronics, Vol. 14, No. 1, 171-179 (2008)

When the PAT technique is used, information on local light absorption can be obtained by measuring acoustic waves generated due to absorption of light at a local inspection target portion. An initial acoustic pressure P is represented by Expression (1) below using a distance r between a light irradiation point to the inspection target portion.

$$P(d) = \Gamma \mu_a(r) \Phi(r) \quad \text{Expression (1)}$$

where $\Gamma$ denotes a Gruneisen coefficient (heat-acoustic conversion efficiency), $\mu_a(r)$ denotes an absorption coefficient in a position corresponding to the distance r, and $\Phi(r)$ denotes a light intensity in the position corresponding to the distance r. The Gruneisen coefficient $\Gamma$ serving as an elastic characteristic value is obtained by dividing a product of a square of a thermal expansion coefficient $\beta$ and a square of an acoustic velocity c by a constant pressure specific heat Cp. Since the value $\Gamma$ is substantially a constant value for the same living tissues, when change of acoustic pressures P serving as amounts of acoustic waves is measured in a time division manner, a product of the values $\mu_a$ and $\Phi$, that is, an optical-energy absorption density distribution H is obtained. Furthermore, $\mu_a(r)$ is obtained by dividing the optical energy absorption density distribution H by the light intensity $\Phi(r)$.

Here, a pulse laser used to generate photoacoustic waves may not generate pulsed light of a constant light quantity due to a fundamental function thereof, and temporal output fluctuation occurs to some degree. Specifically, the light quantity fluctuation may reach 10% or more. When the quantity of the pulsed light is varied, a light quantity $\Phi(r)$ in a local region included in an inspection target is also varied. As described above, since the light quantity $\Phi(r)$ and the intensity P of a photoacoustic wave have the proportional relationship, the photoacoustic waves similarly varies for individual laser pulses. Accordingly, when the optical energy absorption density H distribution and the absorption coefficient $\mu_a$ distribution are imaged, unevenness of intensity occurs in a screen obtained after reconstruction and a quantitative performance of measurement may be deteriorated.

However, Patent Literature 1 above does not include a description relating to temporal output fluctuation of a light source. Furthermore, although Non Patent Literature 1 discloses a technique of correcting a light quantity using a sensor which is used to measure a pulsed-light quantity, a measurement method, usage, and a correction target are not clearly described. Especially, since the description of Non Patent Literature 1 has been made on the assumption that a photoacoustic microscope is used, light attenuation in a depth direction which is important for measurement of a thick inspection target is not clearly described.

The present invention has been made in view of the background technique and recognition of the problem described above. An object of the present invention is to provide a photoacoustic apparatus capable of reducing an adverse effect on an image caused when a quantity of light output from a light source varies with time.

SUMMARY OF INVENTION

To address the above problem, the present invention provides a photoacoustic apparatus including a light source which irradiates an inspection target with pulsed light, a detector which detects acoustic waves generated in the inspection target due to interaction of the pulsed light with the inspection target, and outputs detections signals corresponding to the detected acoustic waves, a light-quantity measurement unit which measures a quantity of light output from the light source, and a signal processor which processes the detection signals output from the detector so as to obtain information on an inside of the inspection target. The signal processor includes a signal correction unit which corrects intensities of the detection signals in accordance with a temporal change in the quantity of light measured by the light-quantity measurement unit so that variations of the intensities of the detection signals are suppressed.

Further features of the present invention will become apparent to persons having ordinary skill in the art from the following description of exemplary embodiments with reference to the attached drawings.

BRIEF DESCRIPTION OF DRAWINGS

FIG. 5 is a diagram schematically illustrating a configuration of a photoacoustic apparatus according to a second embodiment of the present invention.

FIG. 6 is a flowchart illustrating an example of a process of determining correction amounts of intensities of detection signals according to the second embodiment of the present invention.

DESCRIPTION OF EMBODIMENTS

Figure 1:
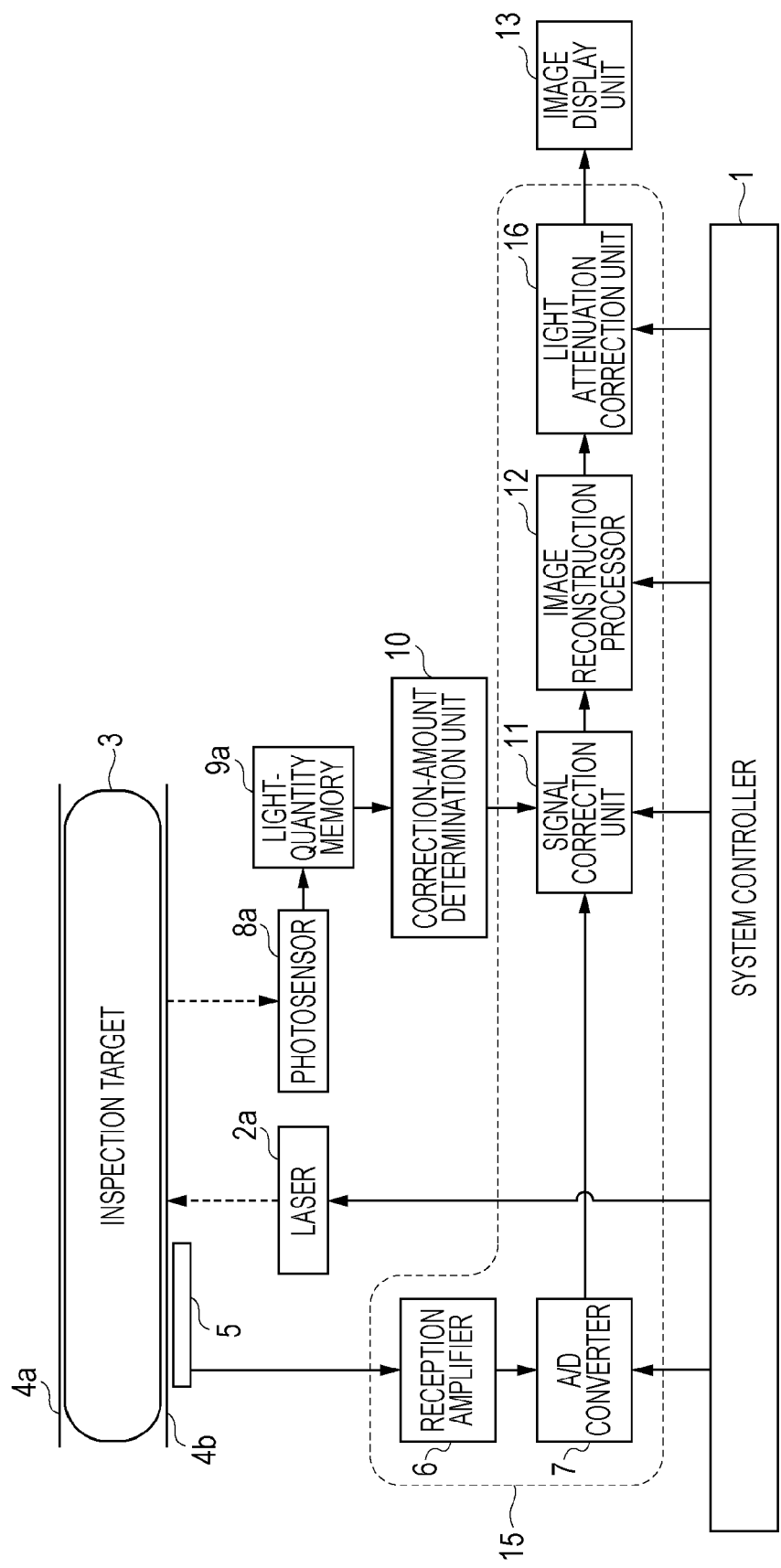
FIG. 1 is a diagram schematically illustrating a configuration of a photoacoustic apparatus according to a first embodiment of the present invention.

Hereinafter, the present invention will be described with reference to the accompanying drawings. Note that the same components are basically denoted by the same reference numerals and redundant descriptions thereof are omitted.

First Embodiment: Photoacoustic Apparatus

First, a configuration of a photoacoustic apparatus according to this embodiment will be described with reference to FIG. 1.

The photoacoustic apparatus of this embodiment corresponds to a photoacoustic imaging apparatus which images information on an inside of an inspection target. When the inspection target is a living body, the photoacoustic apparatus enables imaging of information on the living body in order to perform diagnosis of a malignant tumor or a blood vessel disease and follow-up of chemical treatment. The "information on an inside of an inspection target" in the present invention corresponds to information on a distribution of sources which generated acoustic waves in response to light irradiation, and includes information on a distribution of initial acoustic pressures in the living body, information on an optical energy absorption density distribution obtained from the information on a distribution of initial acoustic pressures, and information on a density distribution of a substance included in a living tissue obtained from the information on a distribution of initial acoustic pressures in the living body and the information on optical energy absorption density distribution obtained from the information on a distribution of initial acoustic pressures. For example, the density distribution of a substance corresponds to oxygen saturation.

The photoacoustic apparatus of this embodiment includes a pulsed laser 2a, a detector 5, and a photosensor 8a as a basic hard configuration. The pulsed laser 2a is a light source used to irradiate the inspection target with pulsed light. It should be noted that in place of the pulsed laser 2a, a different light source (e.g., a modulated light source or energy beam) capable of generating pulses of light may be used.

An inspection target 3 such as a living body is fixed to plates 4a and 4b which presses and fixes the inspection target 3 from both sides of the inspection target 3 where appropriate. Light emitted from the light source is guided to a surface of the plate 4b by an optical system (not shown) including a lens, a mirror, and an optical fiber so that the inspection target is irradiated with the light. When part of light energy propagated through the inspection target 3 is absorbed by an optical absorber such as blood vessels, the optical absorber generates acoustic waves (typically, ultrasonic waves) due to thermal expansion. These acoustic waves may be referred to as "photoacoustic waves". That is, a temperature of the optical absorber is increased due to absorption of pulsed light, the increased temperature causes volume expansion, and accordingly, photoacoustic waves are generated. Here, the duration (length) of a light pulse preferably corresponds to a degree in which a heat/stress sealing condition is satisfied so that absorption energy is efficiently sealed in the optical absorber. Typically, the duration of a light pulse may range from approximately 1 nanosecond to approximately 0.2 seconds, but it is not limited thereto. Persons having ordinary skill in the art may derive appropriate light pulse lengths corresponding to the type of optical absorber which can provide a heat/stress sealing condition so that absorption energy is efficiently sealed in the optical absorber of interest.

A detector 5 used to detect acoustic waves detects the acoustic waves generated in the inspection target and converts the acoustic waves into analog electric signals (detection signals). The detection signals obtained from the detector correspond to the detected acoustic waves and for this reason are referred to as "photoacoustic signals" where appropriate.

A signal processor 15 which processes the photoacoustic signals so as to obtain information on an inside of the inspection target 3 includes a reception amplifier 6, an A/D converter 7, a signal correction unit 11, an image reconstruction processing unit 12, and an optical attenuation correction unit 16 in this embodiment. The photoacoustic signals obtained from the detector 5 are amplified by the reception amplifier 6 and converted into digital photoacoustic signals by the A/D converter 7. The signal correction unit 11 which is one of the characteristic components of this embodiment performs correction of intensities of the digital signals. The image reconstruction processing unit 12 performs calculation processing on three-dimensional information, the optical attenuation correction unit 16 performs correction on obtained voxel data taking light attenuation in the inspection target into consideration. A resulting photoacoustic image of the inspection target is displayed in an image display unit 13 where appropriate. Furthermore, all the components are controlled by a system controller 1. Here, the "photoacoustic image" is obtained by representing the obtained information on the inside of the inspection target by a coordinate in a three-dimensional space and converting the information into luminance information.

Next, characteristic portions of the first embodiment will be described below. A quantity of light output from the laser 2a is measured by the photosensor 8a serving as a light-quantity measurement device. When the quantity of light output from the laser 2a varies with time, this variation is also measured by the photosensor 8a. Then, the signal correction unit 11 corrects intensities of the photoacoustic signals so as to suppress variations of the intensities of the photoacoustic signals. That is, the variations of the intensities of the photoacoustic signals caused by the variation of the quantity of output light with time (temporal change) can be reduced.

Light Source and Variation of Quantity of Light Output from Light Source

Figure 2:
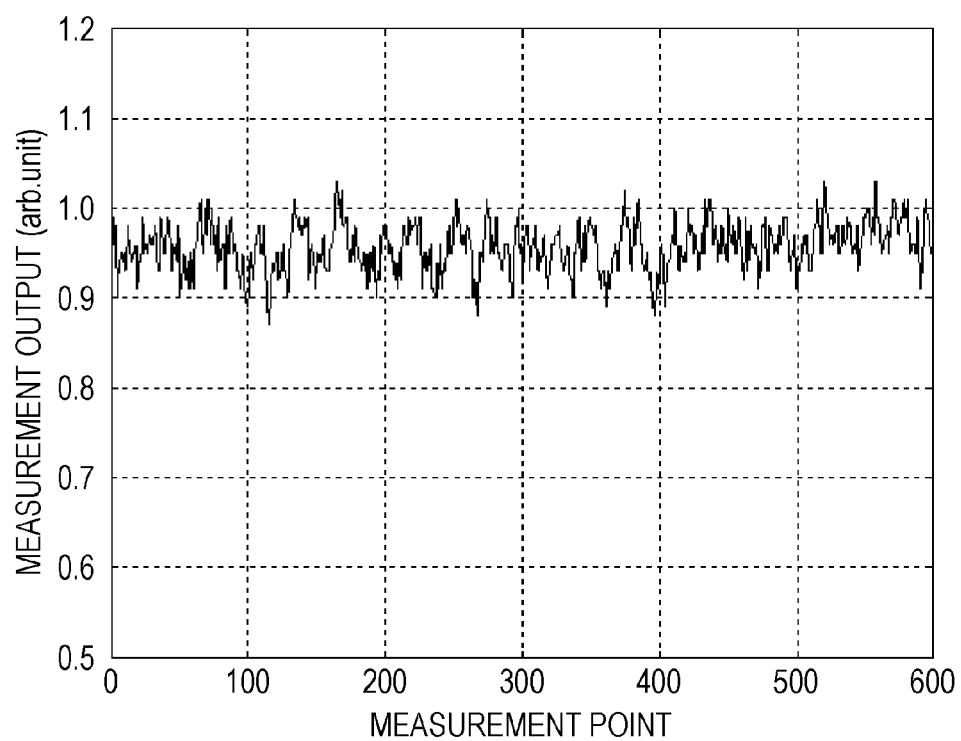
FIG. 2 is a diagram illustrating output fluctuation of laser pulses.

The laser light generated by the laser 2a varies with respect to each pulse. An example of light quantity variation is shown in FIG. 2. In FIG. 2, a temporal change of a measurement output obtained when a YAG laser of approximately 5 W (500 mJ) generates pulsed light of 10 Hz for 60 seconds is measured. According to FIG. 2, the output light quantity having light quantity variation of approximately 10% is recognized.

When the inspection target is a living body, the light source emits light having a specific wavelength which is absorbed by a specific constituent among constituents included in the living body. A pulse light source capable of generating pulsed light of 1 nanosecond order to 0.2 nanoseconds order is preferably used as the light source. Although a laser is preferably used as the light source, a light-emitting diode may be used instead of the laser. Examples of the laser include a solid-state laser, a gas laser, a dye laser, and a semiconductor laser.

Note that the variation of the output light quantity of the laser shown in FIG. 2 is supposed to be mainly caused by variation of a light quantity of a flash lamp serving as a laser excitation light source. Therefore, when the flash lamp or a laser generated from the flash lamp serving as the excitation light source is used as the light source of the present invention, an effect of the present invention is efficiently obtained. However, as noted above, the light source of the present invention is not limited to these sources, and a semiconductor laser or a light-emitting diode which does not include a flash lamp may employ the present invention as long as the light source generates the light quantity variation.

Note that, although an example of a case where a single light source is employed is described in this embodiment, a plurality of light sources may be used, as described below in reference to FIG. 5. When a plurality of light sources are used, the light sources which oscillate in the same wavelength may be used in order to increase an intensity of light emitted to the living body. Alternatively, light source having different oscillation wavelengths may be used in order to measure differences among optical characteristic value distributions depending on wavelengths. Note that, if pigments in which oscillation wavelengths can be changed or OPOs (Optical Parametric Oscillators) is used as light sources, differences among optical characteristic value distributions depending on wavelengths can be measured. A wavelength to be used is selected from a wavelength band in a range from 700 nm to 1100 nm which is merely absorbed in the living body. Note that, when an optical characteristic value distribution of living tissues comparatively in the vicinity of a surface of the living body is to be obtained, a wavelength is selected from a wavelength band in a range from 400 nm to 1600 nm which is larger than the above wavelength band.

The light emitted from the light source may be propagated using an optical waveguide where appropriate. Although not shown in FIG. 1, an optical fiber is preferably used as the optical waveguide. When an optical fiber is used, a plurality of optical fibers may be used for each light source so as to guide light to the surface of the living body. Alternatively, light beams emitted from a plurality of light sources may be guided to a single optical fiber so that all the light beams are guided to the living body only using the single optical fiber. Furthermore, light may be guided by an optical member such as a mirror which mainly reflects light or a lens which collects and enlarges light and which changes a shape of the light. Any optical member may be used as long as light emitted from a light source is encountered on a light irradiation region included in the surface of the inspection target in a desired shape.

First Correction of Detection Signals

Correction of detection signals according to this embodiment will be described in detail hereinafter.

A case where the inspection target is fixed on the plates as shown in FIG. 1, the region in which the laser 2a irradiates with light is set on the surface of the inspection target in a two-dimensional manner, and the light irradiation region is sufficiently larger than an imaging range will be described as an example. A quantity of pulsed light emitted onto the surface of the inspection target is represented by $\Phi_0$. In the inspection target, light in portions farther than the surface is attenuated in an exponential manner due to absorption and scattering. That is, the following expression is obtained:

$$\Phi(r)=\Phi_0 \cdot \exp(-\mu_{eff} \cdot r) \qquad \text{Expression (2)}$$

where µeff denotes an average effective attenuation coefficient of the inspection target. According to Expressions (2) and (1), the following expression is obtained.

$$P(r)=\Gamma\mu_a(d)\Phi_0 \cdot \exp(-\mu_{eff} \cdot r) \qquad \text{Expression (3)}$$

In the present invention, a problem arises in that the value $\Phi_0$ varies with respect to pulses. For example, when a first pulse has an output light amount $\Phi_{01}$ and a second pulse has an output light amount $\Phi_{02}$ which is equal to 0.9 $\Phi_{01}$, an acoustic pressure $P_2(r)$ of a photoacoustic wave generated by the second pulse is equal to 0.9 $P_1(r)$.

Therefore, since an image ($\mu_a$ distribution) of the inside of the inspection target generated from the first pulse and an image generated from the second pulse have different luminance signals relative to the acoustic pressures, image reproducibility is not obtained. Accordingly, when the same portion is measured several times, information on the inside of the inspection target is misrecognized due to deterioration of the image reproducibility. Furthermore, when measurement is performed while the surface of the inspection target is scanned using a laser and a detector, a single image is generated using acoustic pressures obtained in response to a plurality of pulses. In this case, unevenness of luminance occurs in the image due to the light quantity variation described above, and this also causes misrecognition of the information on the inside of the inspection target.

Therefore, in this embodiment, output light quantities $\Phi_{0n}$ of pulses are measured using the photosensor 8a. Then, intensities of detection signals of photoacoustic waves are corrected so that acoustic pressures $P_n(r)$ are supposed to be normally obtained in accordance with a reference light quantity such as a constant initial light quantity $\Phi_0$. In the foregoing example, assuming that the acoustic pressure $P_1(r)$ is used as a reference and an intensity corresponding to 1/0.9 an acoustic pressure $P_2(r)$ is obtained, detection signals are corrected. By this, even when outputs of the light source vary with time, influence cased by the variation can be reduced and information on positions of sound sources and acoustic pressures can be obtained.

Note that, an inverse number of a ratio of the output light quantity $\Phi_{02}$ of the second pulse to the output light quantity $\Phi_0$ of the first pulse, that is, $\Phi_{01}/\Phi_{02}$ is referred to as a "correction coefficient" in this specification. Furthermore, the correction of detection signals described above may be performed on analog signals and digital signals. However, in this embodiment, the correction is performed on amounts converted into digital signals by the A/D converter 7. When digital signals are to be corrected, since the A/D converter 7 outputs values of the acoustic pressures $P(r)$ for individual sampling frequencies, the correction is performed by multiplying a digital signal representing an acoustic pressure $P(r)$ corresponding to a certain pulse by a correction coefficient of the pulse.

Hereinafter, further details are described. In this embodiment, after the photosensor 8a detects a pulse light quantity of the laser 2a for each pulse, the pulse light quantity is stored in a light-quantity memory 9a. Such a memory used to store an output light quantity is preferably provided in terms of reliability of signal processing. A correction-amount determination unit 10 reads data indicative of a temporal change in the output light quantity stored in the light-quantity memory 9a, and determines correction amounts (correction coefficients) for the detection signals. In accordance with the determined correction amounts, the signal correction unit 11 corrects intensities of the detection signals.

Figure 3:
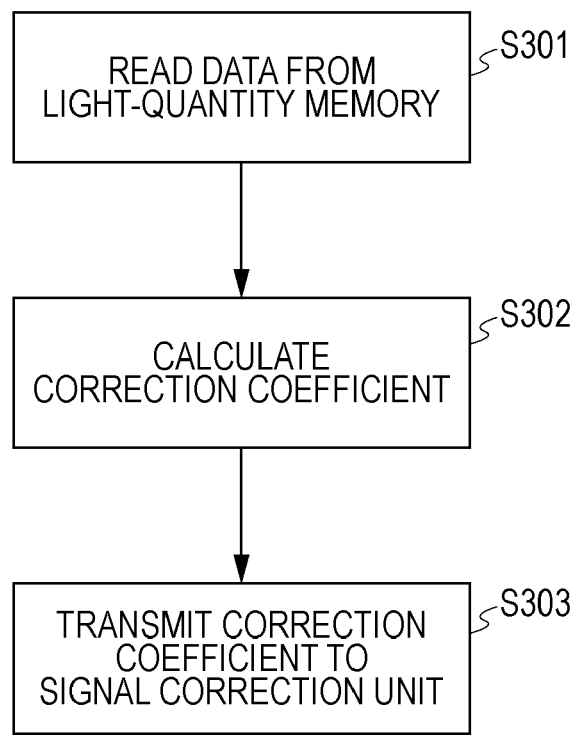
FIG. 3 is a flowchart illustrating an example of a process of determining correction amounts of intensities of detection signals according to the first embodiment of the present invention.

FIG. 3 is a processing flow of correction amount calculation. The correction-amount determination unit 10 reads data from the light-quantity memory 9a (in step S301). In accordance with light quantities of pulses obtained from the light-quantity memory 9a, correction coefficients for the pulses are calculated (in step S302). A light quantity measured in advance is used as a reference value for the correction coefficients. In this specification, a set of correction coefficients of a plurality of pulses is referred to as a "correction amount table". Then, the correction amount table is transmitted to the signal correction unit 11 (in step S303) where obtained photoacoustic signals are calculated using the correction amount table. That is, digital signals of acoustic pressures $P(d)$ obtained for individual sampling frequencies are multiplied by the correction coefficients.

Image Reconstruction and Optical Attenuation Correction

The image reconstruction processing unit 12 performs image reconstruction on the digital signals which have been corrected as described above. The image reconstruction of the PAT is performed to obtain a distribution $P_0(r)$ of initial acoustic pressures generated in the inspection target from acoustic pressures $P_d(r_d, t)$ received by the detector, and is referred to as an "inverse problem" in the mathematical field. A universal back projection (UBP) method representatively used as the image reconstruction method of the PAT has been described in Physical Review E 71, 016706 (2005) and Review of Scientific Instruments, 77, 042201 (2006).

As described above, the distribution of initial acoustic pressures serving as the information on the inside of the inspection target and a product of the value $\mu_a$ and the value $\Phi$, that is, an optical energy absorption density distribution H are obtained. Assuming that the value $\Phi$ is a constant value, when a value H is divided by the value $\Phi$, a distribution of absorption coefficients $\mu_a(r)$ in the inspection target is obtained. However, since a quantity of light emitted to a local region of the inspection target attenuates in an exponential manner as described above, when two tissues have the same absorption coefficient, an acoustic pressure of an acoustic wave generated from one of the tissues which is located farther from the surface of the inspection target is smaller than that of the other tissue which is located nearer the surface of the inspection target. Therefore, in order to obtain a reliable absorption coefficient distribution, such influence of light attenuation is preferably corrected. This correction is referred to as "light attenuation correction" in this specification.

Specifically, the optical attenuation correction unit 16 performs a process of dividing voxel data items representing the absorption density distribution H of optical energy output from the image reconstruction processing unit 12 by corresponding light quantities in positions of the voxels. The light quantities in the positions of the corresponding voxels are calculated by Expression (2) above.

With this configuration, a reliable absorption coefficient distribution in the inspection target can be imaged taking the influence of the optical attenuation into consideration.

Example of First Signal Correction

Note that although a case where correction for light quantity variations with respect to pulses is performed on data which corresponds to digital signals obtained by the A/D converter 7 and has not been subjected to the image reconstruction processing is described in this embodiment, the present invention is not limited to this. The correction may be performed on voxel data which has been subjected to the image reconstruction processing. That is, correction of photoacoustic signals may be similarly performed by inputting the correction coefficients calculated by the correction-amount determination unit 10 to the optical attenuation correction unit 16 so that correction calculation is performed. Furthermore, the correction may be performed on analog data which has not been subjected to the A/D conversion. In this case, a method for controlling a gain of the reception amplifier 6 using an output from the correction-amount determination unit 10 may be employed. That is, the "detection signals" in this specification includes analog signals, digital signals obtained through the A/D conversion, and luminance data obtained by performing the image reconstruction on the digital data.

Furthermore, if a light quantity distribution in the inspection target obtained when light is emitted can be set, when light is emitted from opposite sides of the plate 4 or when light is emitted from various directions, the correction of photoacoustic signals can be similarly performed.

Moreover, although the photoacoustic signals are obtained in a state in which the detector 5 and the laser 2a are fixed in the foregoing embodiment, even when photoacoustic signals are obtained while scanning is performed using the detector 5 and the laser 2a, the correction of photoacoustic signals can be similarly performed by obtaining light-quantity measurement data in various scanning positions.

In addition, the laser pulse 2a to be used is a laser beam having a certain width. When spatial unevenness of an intensity of a section of the laser beam occurs, the correction of photoacoustic signals can be similarly performed by calculating correction light quantities in a three-dimensional space taking the light quantity distribution into consideration.

Detailed Descriptions of Configurations

The detector (probe) 5 detects acoustic waves such as sonic waves and ultrasonic waves and converts the acoustic waves into electric signals. Any acoustic wave detector such as a transducer utilizing piezoelectric phenomenon, a transducer utilizing optical resonance, or a transducer utilizing change of capacitance may be used as long as the acoustic wave detector can detect acoustic wave signals. The detector 5 in this embodiment is preferably an array type detector having a plurality of transducer elements. When the transducer elements arranged in a two-dimensional manner are used, acoustic waves are simultaneously detected in a plurality of portions. Accordingly, a period of time required for the detection can be reduced and influence of vibration of the inspection target can be reduced. Furthermore, an acoustic impedance matching agent such as gel or water is preferably used between the detector 5 and the plate 4b and between the plate 4b and the inspection target 3 so as to suppress reflection of acoustic waves.

Examples of a typical light-quantity measurement device include a photosensor as typified by a photodiode and a pyroelectric sensor. When a one-dimensional or a two-dimensional photosensor array is required, a CCD image sensor, a CMOS image sensor, a light dependent resistor (LDR), or the like may be used to obtain a similar effect.

A preferable arrangement of the photosensor 8a serving as the light-quantity measurement device will be described with reference to FIGS. 4A to 4C. A reference numeral 18 denotes a reflection mirror and a reference numeral 19 denotes a laser beam of pulsed light.

Figure 4A:
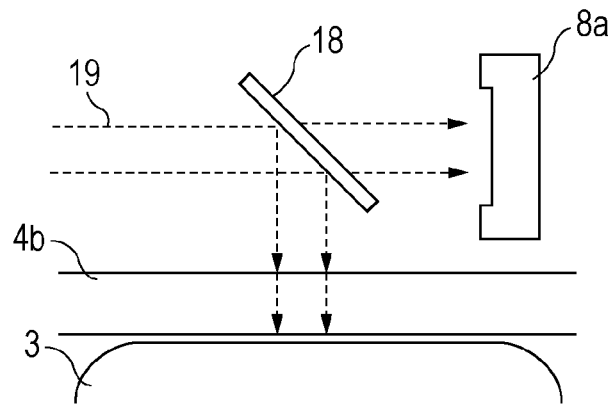
FIGS. 4A to 4C are diagrams illustrating arrangements of a photosensor according to the present invention.

FIG. 4A shows a case where light leaked from a reflection mirror disposed in the optical system is detected before light reaches the plate 4b. As shown in FIG. 4A, since the photosensor 8a is disposed after the reflection mirror, part of the light emitted from the light source can be detected. If a rate of the leakage light is known in advance, variation of quantities of light emitted from the light source can be calculated.

Figure 4B:
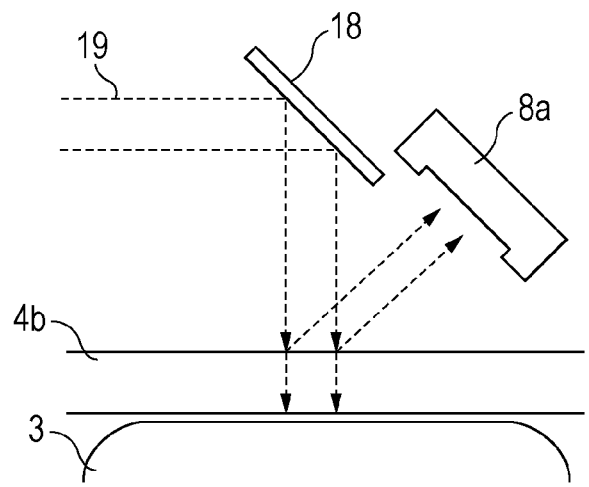

FIG. 4B shows a case where part of light reflected by the plate 4b is detected. As shown in FIG. 4B, the photosensor 8a may be disposed in the vicinity of the plate 4b.

Figure 4C:
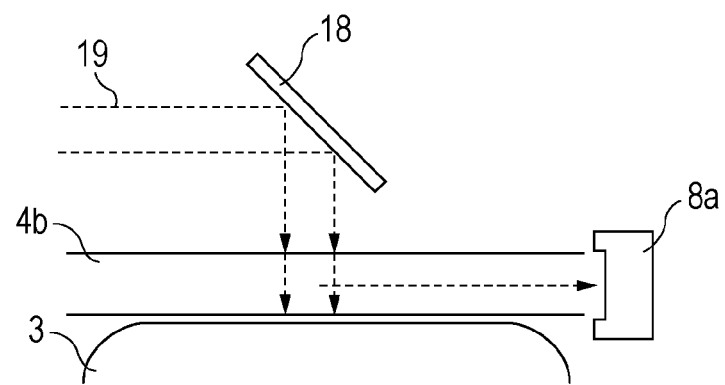

FIG. 4C shows a case where part of light which has been propagated inside the plate 4b is detected. As shown in FIG. 4C, the photosensor 8a may be disposed at an end portion of the plate 4b. Especially, when light is obliquely entered relative to the plate 4b, light propagated inside the plate 4b is increased, which is preferable.

As a memory, a memory included in a PC or a control board may be employed. However, a similar effect can be obtained when a memory attached to a photosensor unit is used or a hard disk is used as long as a speed higher than a laser pulse cycle is ensured.

First Example

Hereinafter, as a first example, a case where the photoacoustic apparatus according to the present invention is employed in a breast examination will be described in detail. In the breast examination of this example, breast compression similar to that generally performed in X-ray mammography is performed. That is, in the breast, photoacoustic signals within a depth of 4 cm which is an average thickness of the breast compression should be obtained.

In this embodiment, as the light source, a Q switch YAG laser which has a wavelength of 1064 nm, which is driven in 10 Hz, which has a pulse width of 5 nanoseconds, and which has an output per pulse of 1.6 J is used. Under this condition, since a human body allows to be irradiated with laser light having an intensity of 100 mJ/cm2 or smaller according to JIS, an illumination optical system which enlarges emitted laser light to square 4 cm on a side is designed.

Then, it is assumed that a range in which photoacoustic signals are generated in response to light emitted from both sides of the breast while the breast is compressed has a depth of 4 cm and a width of 4 cm. Furthermore, in order to obtain the photoacoustic signals within this range, an ultrasonic transducer has 4 cm on a side. Furthermore, a two-dimensional probe having 400 elements is configured while an element pitch is set to 2 mm. In addition, a frequency of 1 MHz is used. A PIN photodiode S5973 manufactured by Hamamatsu Photonics K.K. is used as a photosensor.

When photoacoustic signals are to be obtained under the condition described above, a quantity of irradiated light obtained at a time of laser irradiation is normally stored in a light-quantity memory. Correction coefficients for pulses are calculated using the maximum value of a measured light-quantity variation of 1. Correction of detection signals is performed in accordance with the correction method described with reference to the configuration shown in FIG. 1. A photoacoustic image generated through image reconstruction is stored as volume data and displayed in a screen.

Although unevenness of an intensity of the photoacoustic image can be improved using this method, since reproducibility of the photoacoustic signals based on electric noise is approximately 2% to approximately 3% and unevenness of distribution of irradiated light is approximately 2%, unevenness of an image remains in a similar degree. However, when this method is employed, the unevenness of image of approximately 8% to approximately 10% can be reduced to approximately 3% to 4%.

Note that distribution of irradiated light can be measured by additionally disposing a CCD sensor or the like in an optical path. The reproducibility of the photoacoustic signals can be measured by operating this system in a state in which laser irradiation is not performed. The image unevenness is defined to be three times standard deviation of luminance value variation at the same pixel obtained when image capturing is performed a plurality of times.

Note that, although the case where the photoacoustic apparatus is used for the breast examination is described in detail in this embodiment, similar effects are obtained when the other portions of the human body and inspection bodies other than a human body are measured by similar processing.

Second Embodiment

In the first embodiment, the laser light is emitted only from one side. In a second embodiment, a correction method employed when laser light is emitted from opposite sides of a plate 4 will be described. FIG. 5 shows an example of a photoacoustic apparatus according to this embodiment. Irradiation of laser pulses, light-quantity data, and photoacoustic signals are obtained similarly to the first embodiment. This embodiment is different from the first embodiment in that the laser light is emitted from opposite sides, that is, from lasers 2a and 2b and outputs of the lasers 2a and 2b are detected by photosensors 8a and 8b, respectively. It should be noted that although the laser sources 2a and 2b and corresponding photosensors 8a and 8b are shown as separate elements for ease of illustration, the lasers sources can be part of a single laser source and the photosensors can be part of a single photosensor array. Accordingly, it can be said that a light source may include a plurality of light sources, and that a light-quantity measurement unit may include a plurality of light-quantity measurement units. Detected light quantities are stored in light-quantity memories 9a and 9b and transmitted to correction-amount determination units 10a and 10b. Then, two correction coefficients are calculated using a method similar to that of the first embodiment, and the correction coefficients are transmitted to a signal correction unit 11.

Processes performed by the correction-amount determination units 10a and 10b and a processes performed by a signal correction unit 11 will be described in detail with reference to FIG. 6. Correction coefficients for light quantities of lasers obtained from the light-quantity memories 9a and 9b (in step S601) are calculated by setting the maximum value of light-quantity variations measured in advance to 1 (in step S602). Then, relative attenuation amounts in a depth direction are calculated using standardized light quantities and the coefficients so that two correction-amount tables are generated using two light-quantity data items (in step S603). The correction-amount tables in the depth direction are added to each other relative to the same depth so that a synthesized correction-amount table is generated (in step S604).

That is, acoustic pressures obtained in accordance with light emitted from one side of the plate 4 is represented similarly to Expression (3) described above.

$$P(r)=\Gamma\mu_a(r)\Phi_{0A}\cdot\exp(-\mu_{eff}\cdot r) \quad \text{Expression (3)}$$

However, an acoustic pressure obtained in accordance with light emitted from the other side is represented by the following expression.

$$P(r)=\Gamma\mu_a(r)\Phi_{0B}\cdot\exp(-\mu_{eff}\cdot(D-r)) \quad \text{Expression (4)}$$

Here, D denotes a distance between the compression plates 4a and 4b, and $\Phi_{0A}$ denotes an initial light quantity obtained after pulsed light emitted from the laser 2a is multiplied by a corresponding one of the correction coefficients of the light quantity variations. Furthermore, $\Phi_{0B}$ denotes an initial light quantity obtained after pulsed light emitted from the laser 2b is multiplied by a corresponding one of the correction coefficients of the light quantity variations. Each of the correction-amount tables is obtained by quantifying the light quantity in the above expression and light attenuation in accordance with a sampling frequency and adding them with each other, and therefore, is represented by the following expression.

$$C(r)=1/(\Phi_{0A}\cdot(\exp(-\mu_{eff}\cdot r)+\Phi_{0B}\exp(-\mu_{eff}\cdot(D-r)))) \quad \text{Expression (5)}$$

Here, C(r) denotes values of the correction-amount tables, $\Phi_{0A}$, $\Phi_{0B}$, r, D, and $\mu_{eff}$ can be obtained since they are known in advance. Then, synthesized correction-amount table C(d) is multiplied by obtained image reconstruction data (in step S605). At this time, the correction-amount tables are functions in the depth direction (a straight-line distance from a surface of an inspection target). On the other hand, the image reconstruction data is three-dimensional data but multiplication is performed only in the depth direction and a certain process is performed in a height and width direction (in an in-plane direction of the surface of the inspection target). Thereafter, a photoacoustic image is stored as volume data and displayed in a screen. With this method, a process of correcting digital data which has been subjected to the image reconstruction taking the variations of quantities of light supplied from a light source into consideration and a process of correcting digital data which has been subjected to the image reconstruction taking light attenuation in the depth direction into consideration are collectively performed. In this case, detection signals may be acoustic pressure signals which have been converted into luminance signals.

According to this embodiment, as with the first embodiment, even when the light is emitted from opposite sides of the plate 4, image unevenness can be improved.

Third Embodiment

In the first and second embodiments, the intensities of the photoacoustic signals are corrected assuming that the surface of the inspection target is irradiated with the constant light quantity $\Phi_0$ irrespective of portions. In a third embodiment, a correction method employed when intensity distribution of initial light quantities is generated on a surface to which a laser is encountered (a surface of an inspection target) will be described.

Figure 7:
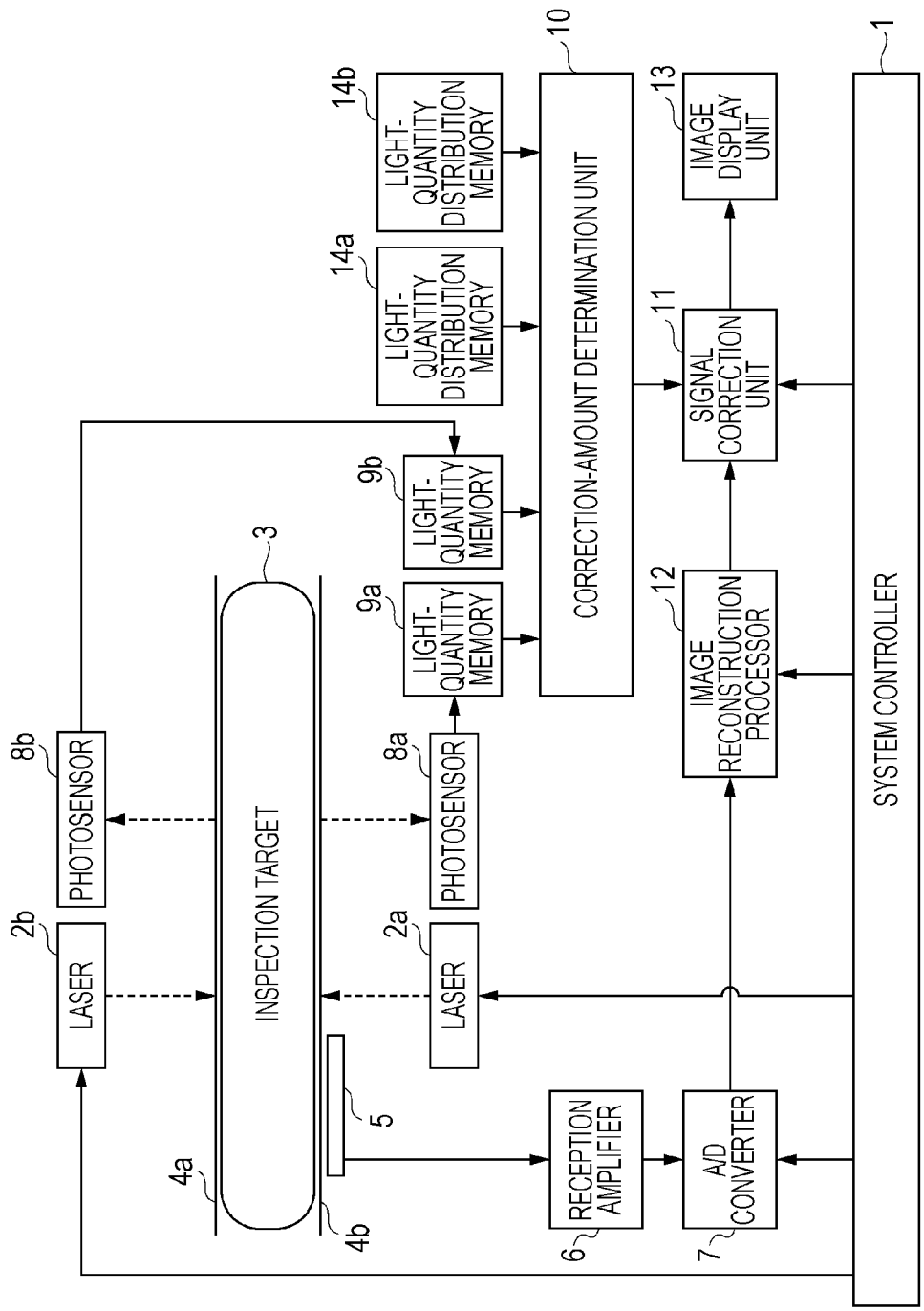
FIG. 7 is a diagram schematically illustrating a configuration of a photoacoustic apparatus according to a third embodiment of the present invention.

FIG. 7 shows an example of a photoacoustic apparatus of this embodiment. Emission of laser pulses and obtainment of light-quantity data and photoacoustic signals are performed similarly to the second embodiment. Laser to be emitted to an inspection target 3 is enlarged to square 4 cm on a side which is the same as a detector 5 and is emitted. Intensity distribution is included in a plane. This is especially observed when a multimode laser is used. The in-plane intensity distribution is measured in advance and stored in light-quantity distribution memories 14a and 14b.

Note that a correction amount used for correction is obtained by reflecting the light intensity distribution. That is, the correction amount corresponds to a function of the initial light quantity and an attenuation coefficient obtained by multiplying the light intensity distribution, a Gruneisen coefficient, an absorption coefficient, and a correction coefficient, and is calculated using light propagation simulation since the light intensity distribution is not analytically obtained. A light-quantity distribution in a three-dimensional direction is obtained through the calculation, and Expression (3) is replaced by the following expression:

$$P(r)=\Gamma\mu_a(d)\Phi_0(x,y,r,t)\cdot\exp(-\mu_{eff}\cdot r) \quad \text{Expression (6)}$$

where a light quantity $\Phi_0(x, y, r, t)$ corresponds to a function of a space (x, y, r) distribution and each pulse oscillated every time period t. This light quantity $\Phi_0$ is calculated through the simulation, and after coefficients are multiplied, inversed numbers are obtained whereby correction coefficients in portions in the three-dimensional space are obtained.

The correction-amount calculation of this embodiment is excellent in that signal correction is performed taking, in addition to light-quantity variations with time, spatial irradiation light quantity distribution in a surface of the inspection target into consideration. Reproducibility of the photoacoustic signals is the same as that of the first embodiment. When a photoacoustic image is obtained and corrected taking these factors into consideration, unevenness of an intensity of the photoacoustic image which is 8% to 10% in a state in which the light-quantity distribution correction has not been performed can be reduced to approximately 3%, that is, reduced to a degree substantially the same as the reproducibility of the photoacoustic signals.

Fourth Embodiment

In the first to third embodiments, the photoacoustic signals are obtained while the detector 5 and the laser 2a are fixed. In a fourth embodiment, a case where photoacoustic signals are obtained while a detector 5 and a laser 2a are moved along a plate 4 for scanning.

A system configuration is shown in FIGS. 4A to 4C. However, in this embodiment, a movement mechanism which moves the laser 2a, a laser 2b, and the detector 5 relative to an inspection target is provided. Note that as long as a light incidence portion of the inspection target in which light is incident from a light source is scanned, the lasers themselves are not required to be moved for scanning. In this case, a light-quantity variation generated during the scanning which is not taken into consideration in the first to third embodiments should be corrected.

Assuming that breast is scanned using the light source and the ultrasonic transducer described above, a scanning region corresponds to a range of 20 cm×20 cm and a stripe width is 4 cm, and accordingly, a stripe pattern of 4 cm×20 cm is formed five times. Furthermore, a step-and-repeat method, that is, a method for repeating move and stop of the transducer and performing laser irradiation while the transducer is stopped is employed in the scanning performed by the transducer, and in this way, photoacoustic signals are obtained. On the other hand, at a time of laser irradiation, an irradiation light quantity is normally stored in a light-quantity memory.

Standardization of light quantities, calculation processing, and correction of photoacoustic signals are performed similarly to the second embodiment. However, corrected photoacoustic signals are temporarily stored in a memory until scanning is terminated. Then, after the scanning is completely terminated, image reconstruction is performed using the corrected photoacoustic signals, and a generated photoacoustic image is stored as volume data and displayed in a screen.

Intensity unevenness of a photoacoustic image can be improved through this method. Reproducibility of a photoacoustic signals corresponds to approximately 2% to approximately 3% while an S/N ratio is increased four or five times as an effect of averaging of the photoacoustic signals by the scanning. Taking such influence into consideration, image unevenness corresponding to approximately 8% to approximately 10% in a state in which the light-quantity correction has not been performed in conventional scanning is reduced to 1% or less.

Fifth Embodiment

Furthermore, the present invention may be realized by performing the following processing. Specifically, software (a program) which realizes the functions of the foregoing embodiments is supplied to a system or an apparatus through a network or various storage media, and a computer (a CPU, an MPU, or the like) included in the system of the apparatus reads and execute the program.

According to the present invention, a photoacoustic apparatus which includes a light-quantity measurement unit and which corrects intensities of photoacoustic signals taking a temporal change of an output light quantity measured by the light-quantity measurement unit into consideration so that adverse effect of the output fluctuation on an image becomes negligible even when temporal output fluctuation of light output from a light source occurs can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST

1 SYSTEM CONTROLLER
2a, 2b LASER
3 INSPECTION TARGET
4a, 4b PLATE
5 DETECTOR
6 RECEPTION AMPLIFIER
7 ANALOG-DIGITAL CONVERTER
8a, 8b PHOTOSENSOR
9a, 9b LIGHT-QUANTITY MEMORY
10 CORRECTION-AMOUNT CALCULATION UNIT
11 SIGNAL CORRECTION UNIT
12 IMAGE RECONSTRUCTION PROCESSOR
15 SIGNAL PROCESSOR
16 LIGHT ATTENUATION CORRECTION UNIT

The invention claimed is:

1. A photoacoustic apparatus comprising:
a light source configured to irradiate an inspection target with pulsed light;
a detector having a plurality of transducer elements configured to output a plurality of analog signals by detecting an acoustic wave generated due to irradiating the inspection target with the pulsed light;
a light-quantity measurement unit configured to measure a quantity of the pulsed light output from the light source, before the inspection target is irradiated with the pulsed light;
an A/D (analog-to-digital) converter configured to convert the plurality of analog signals output from the plurality of transducer elements into a plurality of digital signals; and
a signal processing unit configured to:
obtain image reconstruction data in a three-dimensional space by performing image reconstruction based on the plurality of digital signals,
obtain a light intensity distribution of the pulsed light in the three-dimensional space by performing a light propagation simulation based on an in-plane light intensity distribution of the pulsed light, an attenuation inside the inspection target of the pulsed light, and the quantity of the pulsed light measured by the light-quantity measurement unit, and
obtain information on an inside of the inspection target in the three-dimensional space by correcting the image reconstruction data in the three-dimensional space based on the light intensity distribution of the pulse light in the three-dimensional space.

2. The photoacoustic apparatus according to claim 1, wherein
the signal processing unit is configured to obtain the image reconstruction data by converting the plurality of digital signals into an initial acoustic pressure distribution or an optical energy absorption density distribution in the three-dimensional space.

3. The photoacoustic apparatus according to claim 1, wherein
the signal processing unit is configured to obtain an absorption coefficient distribution in the three-dimen- 4. The photoacoustic apparatus according to claim 1, wherein
the signal processing unit is configured to obtain an oxygen saturation distribution in the three-dimensional space as the information on the inside of the inspection target in the three-dimensional space.

5. The photoacoustic apparatus according to claim 1, wherein
the signal processing unit is configured to:
determine a correction amount based on a predetermined reference value and the quantity of the pulsed light measured by the light-quantity measurement unit, and
obtain the light intensity distribution in the three-dimensional space based on the correction amount.

6. The photoacoustic apparatus according to claim 5 wherein
the signal processing unit is configured to obtain the light intensity distribution in the three-dimensional space based on the in-plane light intensity distribution of the pulsed light, the attenuation inside the inspection target of the pulsed light, and the correction amount.

7. The photoacoustic apparatus according to claim 1, wherein the light source includes a plurality of light sources,
wherein the light-quantity measurement unit is configured to measure a quantity of the pulsed light output from each of the light sources, and
wherein the signal processing unit is configured to obtain the light intensity distribution in the three-dimensional space based on the quantity of the pulsed light output from each of the light sources and measured by the light-quantity measurement unit.

8. The photoacoustic apparatus according to claim 7,
wherein the signal processing unit is configured to obtain the light intensity distribution in the three-dimensional space based on the quantity of the pulsed light output from each of the plurality of light sources and measured by the light-quantity measurement unit, an in-plane light intensity distribution of the pulsed light output from each of the plurality of light sources, and an attenuation inside the inspection target of the pulsed light output from each of the plurality of light sources.

9. The photoacoustic apparatus according to claim 1, further comprising a mechanism configured to scan an incident position at which the pulsed light is incident on the inspection target and the detector.

10. The photoacoustic apparatus according to claim 1, further comprising:
a memory configured to store the quantity of the pulsed light measured by the light-quantity measurement unit,
wherein the signal processing unit is configured to read the quantity of pulsed light stored in the memory.

11. The photoacoustic apparatus according to claim 1, further comprising:
plates which press and fix the inspection target from opposite sides of the inspection target; and
a mechanism configured to scan an incident position at which the pulsed light is incident on the inspection target and the detector along the plates.

12. The photoacoustic apparatus according to claim 1, wherein the signal processing unit is configured to obtain the information on the inside of the inspection target in the three-dimensional space by correcting the image reconstruction data in the three-dimensional space based on the light intensity distribution of the pulse light in the three-dimensional space so that variations in the image reconstruction data in the three-dimensional space, caused by a temporal change in the quantity of pulsed light, are suppressed.

13. A photoacoustic apparatus comprising:
a light source configured to irradiate an inspection target with pulsed light;
a detector having a plurality of transducer elements configured to output a plurality of analog signals by detecting an acoustic wave generated due to irradiating the inspection target with the pulsed light;
a light-quantity measurement unit configured to measure a quantity of the pulsed light output from the light source, before the inspection target is irradiated with the pulsed light;
an A/D (analog-to-digital) converter configured to convert the plurality of analog signals output from the plurality of transducer elements into a plurality of digital signals; and
a signal processing unit configured to:
obtain image reconstruction data in a three-dimensional space by performing image reconstruction based on the plurality of digital signals,
obtain information on an inside of the inspection target in the three-dimensional space by correcting the image reconstruction data in the three-dimensional space based on a light intensity distribution of the pulse light in the three-dimensional space,
determine a correction amount based on a ratio of a predetermined reference value and the quantity of the pulsed light measured by the light-quantity measurement unit,
wherein the signal processor obtains the light intensity distribution in the three-dimensional space based on an in-plane light intensity distribution of the pulsed light, an attenuation inside the inspection target of the pulsed light, and the correction amount.

14. A photoacoustic apparatus comprising:
a light source configured to irradiate an inspection target with pulsed light;
a detector having a plurality of transducer elements configured to output a plurality of analog signals by detecting an acoustic wave generated due to irradiating the inspection target with the pulsed light;
a light-quantity measurement unit configured to measure a quantity of the pulsed light output from the light source, before the inspection target is irradiated with the pulsed light;
an A/D (analog-to-digital) converter configured to convert the plurality of analog signals output from the plurality of transducer elements into a plurality of digital signals; and
a signal processing unit configured to:
obtain image reconstruction data in a three-dimensional space by performing image reconstruction based on the plurality of digital signals,
obtain information on an inside of the inspection target in the three-dimensional space by correcting the image reconstruction data in the three-dimensional space based on the quantity of the pulsed light measured by the light-quantity measurement unit so that variations in the image reconstruction data in the three-dimensional space, caused by a temporal change in the quantity of pulsed light, are suppressed.

15. The photoacoustic apparatus according to claim 14, wherein the signal processing unit is configured to obtain an initial acoustic pressure distribution or an optical energy absorption density distribution in the three-dimensional space as the image reconstruction data in the three-dimensional space.

16. The photoacoustic apparatus according to claim 14, wherein
the signal processing unit is configured to obtain an absorption coefficient distribution in the three-dimensional space as the information on the inside of the inspection target in the three-dimensional space.

17. The photoacoustic apparatus according to claim 14, wherein
the signal processing unit is configured to obtain an oxygen saturation distribution in the three-dimensional space as the information on the inside of the inspection target in the three-dimensional space.

18. The photoacoustic apparatus according to claim 14, further comprising a mechanism configured to scan an incident position at which the pulsed light is incident on the inspection target and the detector.

19. The photoacoustic apparatus according to claim 14, further comprising:
a memory configured to store the quantity of the pulsed light measured by the light-quantity measurement unit, wherein the signal processing unit is configured to read the quantity of pulsed light stored in the memory.

20. A signal processing method comprising:
obtaining image reconstruction data in a three-dimensional space generated by performing image reconstruction based on a plurality of digital signals obtained by detecting, with a plurality of transducers, an acoustic wave generated due to irradiating an inspection target with a pulsed light;
measuring a quantity of the pulsed light before the inspection target is irradiated with the pulsed light;
obtaining a light intensity distribution of the pulse light in the three-dimensional space by performing a light propagation simulation based on an in-plane light intensity distribution of the pulsed light, an attenuation inside the inspection target of the pulsed light, and the quantity of the pulsed light measured by a light-quantity measurement unit; and
obtaining information on an inside of the inspection target in the three-dimensional space by correcting the image reconstruction data in the three-dimensional space based on the light intensity distribution of the pulse light in the three-dimensional space.

21. The signal processing method according to claim 20, wherein
an oxygen saturation distribution in the three-dimensional space is obtained, as the information on the inside of the inspection target in the three-dimensional space.

22. The signal processing method according to claim 20, further comprising:
determining a correction amount based on a predetermined reference value and the measured quantity of the pulsed light,
wherein the light intensity distribution in the three-dimensional space is obtained based on the correction amount.

23. The signal processing method according to claim 22, wherein
the light intensity distribution in the three-dimensional space is obtained based on the in-plane light intensity distribution of the pulsed light, the attenuation inside the inspection target of the pulsed light, and the correction amount.

24. The signal processing method according to claim 20, further comprising
generating the image reconstruction data in the three-dimensional space by performing the image reconstruction based on the plurality of digital signals.

25. The signal processing method according to claim 20, wherein the information on the inside of the inspection target in the three-dimensional space is obtained by correcting the image reconstruction data in the three-dimensional space based on the light intensity distribution of the pulse light in the three-dimensional space so that variations in the image reconstruction data in the three-dimensional space, caused by a temporal change in the quantity of pulsed light, are suppressed.

26. A signal processing method comprising:
obtaining image reconstruction data in a three-dimensional space generated by performing image reconstruction based on a plurality of digital signals obtained by detecting, with a plurality of transducers, an acoustic wave generated due to irradiating an inspection target with a pulsed light;
measuring a quantity of the pulsed light before the inspection target is irradiated with the pulsed light;
obtain a light intensity distribution of the pulsed light in the three-dimensional space based on the quantity of the pulsed light; and
obtaining information on an inside of the inspection target in the three-dimensional space by correcting the image reconstruction data in the three-dimensional space based on the light intensity distribution of the pulse light in the three-dimensional space;
determining a correction amount based on a ratio of the predetermined reference value and the quantity of the pulsed light measured by a light-quantity measurement unit, and
wherein the light intensity distribution in the three-dimensional space is obtained based on the correction amount.

27. A signal processing method comprising:
obtaining image reconstruction data in a three-dimensional space generated by performing image reconstruction based on a plurality of digital signals obtained by detecting, with a plurality of transducers, an acoustic wave generated due to irradiating an inspection target with a pulsed light;
measuring a quantity of the pulsed light before the inspection target is irradiated with the pulsed light; and
obtaining information on an inside of the inspection target in the three-dimensional space by correcting the image reconstruction data in the three-dimensional space based on the quantity of the pulsed light measured by a light-quantity measurement unit, so that variations in the image reconstruction data in the three-dimensional space, caused by a temporal change in the quantity of pulsed light, are suppressed.

28. The signal processing method according to claim 27, wherein
an initial acoustic pressure distribution or an optical energy absorption density distribution in the three-dimensional space is obtained as the image reconstruction data in the three-dimensional space.

29. The signal processing method according to claim 27, wherein an absorption coefficient distribution in the three-dimensional space is obtained as the information on the inside of the inspection target in the three-dimensional space.

30. The signal processing method according to claim 27, wherein an oxygen saturation distribution in the three-dimensional space is obtained as the information on the inside of the inspection target in the three-dimensional space.

31. The signal processing method according to claim 27, further comprising generating the image reconstruction data in the three-dimensional space by performing the image reconstruction based on the plurality of digital signals.

* * * * *